United States Patent
Riskin

(10) Patent No.: US 12,023,685 B2
(45) Date of Patent: Jul. 2, 2024

(54) METHOD AND DEVICE FOR OZONE-FREE SEPARATION OF COMPONENTS IN THE CORONA DISCHARGE ZONE

(71) Applicant: TADIRAN CONSUMER AND TECHNOLOGY PRODUCTS LTD, Petah Tikva (IL)

(72) Inventor: Yefim Riskin, Petah Tikva (IL)

(73) Assignee: OXYPRO LTD., Ma'alot Tarshiha (IL)

( * ) Notice: Subject to any disclaimer, the term of this patent is extended or adjusted under 35 U.S.C. 154(b) by 0 days.

(21) Appl. No.: 17/639,327

(22) PCT Filed: Jun. 1, 2020

(86) PCT No.: PCT/IL2020/050608
§ 371 (c)(1),
(2) Date: Feb. 28, 2022

(87) PCT Pub. No.: WO2021/038551
PCT Pub. Date: Mar. 4, 2021

(65) Prior Publication Data
US 2022/0314235 A1 Oct. 6, 2022

(30) Foreign Application Priority Data
Aug. 29, 2019 (IL) .......................................... 269021

(51) Int. Cl.
*B03C 3/017* (2006.01)
*A61L 9/22* (2006.01)
(Continued)

(52) U.S. Cl.
CPC .............. *B03C 3/017* (2013.01); *A61L 9/22* (2013.01); *B03C 3/16* (2013.01); *B03C 3/41* (2013.01);
(Continued)

(58) Field of Classification Search
CPC ..... B03C 2201/24; B03C 3/368; B03C 3/383; B03C 2201/06; B03C 3/41; B03C 3/68;
(Continued)

(56) References Cited

U.S. PATENT DOCUMENTS 3,337,784 A * 8/1967 Lueder .................... H01T 23/00
361/231
5,116,583 A 5/1992 Batchelder et al.
(Continued)

FOREIGN PATENT DOCUMENTS

EP 2192662 A2 2/2010
WO 2010123579 A1 10/2010
(Continued)

*Primary Examiner* — Christopher P Jones
*Assistant Examiner* — Sonji Turner
(74) *Attorney, Agent, or Firm* — Richard T. Black; FISHERBROYLES LLP

(57) ABSTRACT

In a method and device for separating components in a corona discharge zone an air stream containing water molecules is passed between at least one ionizing electrode and at least one non-ionizing electrode; and high voltage is applied to the electrodes to create a corona discharge zone consisting of a plasma region wherein ozone is formed and a dark region where predominantly hydrogen peroxide is formed. The air flow entering the corona discharge zone is divided into two separate air flows, a first of which passes through the corona discharge plasma region, and a second of which passes through the dark corona discharge region; and a negative pressure gradient is applied to the plasma region only so as to remove the ozone and thereby separate the ozone from the hydrogen peroxide.

17 Claims, 1 Drawing Sheet

(51) Int. Cl.
*B03C 3/16* (2006.01)
*B03C 3/41* (2006.01)
*B03C 3/49* (2006.01)
*H01J 37/32* (2006.01)

(52) U.S. Cl.
CPC .......... *B03C 3/49* (2013.01); *H01J 37/32073* (2013.01); *A61L 2209/211* (2013.01)

(58) Field of Classification Search
CPC ........... B03C 3/017; B03C 3/155; B03C 3/38; B03C 3/49; B03C 3/60; B03C 3/16; A61L 9/22; A61L 2209/211; A61L 2202/11; A61L 2202/25; A61L 2/14; A61L 2/208; A61L 2209/212; A61L 2209/16; A61L 2/202; A61L 9/015; A61L 11/00; A61L 9/046; A61L 2/10; A61L 2202/26; A61L 2209/10; A61L 9/20; A61L 2/08; A61L 2209/11; A61L 2/24; A61L 2/26; A61L 2202/122; A61L 2202/14; A61L 2202/17; A61L 2209/14; A61L 2/183; A61L 2209/134; A61L 9/032; H01J 37/32073; H01J 37/32348; H01J 61/30; H01J 61/72; H01J 61/16; H05H 2245/15; H05H 1/47; H05H 1/471; H05H 1/2406; F24F 8/30; F24F 8/192; H01T 23/00; H01T 19/04; Y02A 50/20; C01B 13/10; C01B 13/11; C01B 13/115; C01B 13/14; C01B 13/145; C01B 13/16; C01B 15/01; B01D 2257/708; B01D 2257/90; B01D 2257/91; B01D 2259/4508; B01D 2259/818; B01D 53/32; B01D 2255/20707; B01D 2255/802; B01D 2257/106; B01D 2259/804; B01D 53/007; B01D 53/8675; Y10T 29/49117; B65D 90/02
See application file for complete search history.

(56) References Cited

U.S. PATENT DOCUMENTS

| | | | |
|---|---|---|---|
| 6,373,680 B1 | 4/2002 | Riskin | |
| 6,508,982 B1 | 1/2003 | Shoji | |
| 8,048,200 B2 * | 11/2011 | Gefter | B03C 3/49 96/97 |
| 8,167,985 B2 * | 5/2012 | Gefter | B03C 3/155 96/60 |
| 8,325,456 B2 * | 12/2012 | Takayanagi | H01T 23/00 361/231 |
| 8,460,433 B2 * | 6/2013 | Gefter | B03C 3/383 96/97 |
| 9,071,040 B2 | 6/2015 | Mamiya et al. | |
| 9,843,169 B2 | 12/2017 | Riskin et al. | |
| 10,020,180 B2 | 7/2018 | Waddell | |
| 10,128,075 B2 | 11/2018 | Waddell | |
| 2010/0269692 A1 * | 10/2010 | Gefter | B03C 3/017 96/60 |
| 2016/0175803 A1 * | 6/2016 | Riskin | H01T 19/00 422/186.21 |

FOREIGN PATENT DOCUMENTS

| | | |
|---|---|---|
| WO | 2015108344 A1 | 7/2015 |
| WO | 2016197224 A1 | 12/2016 |

* cited by examiner

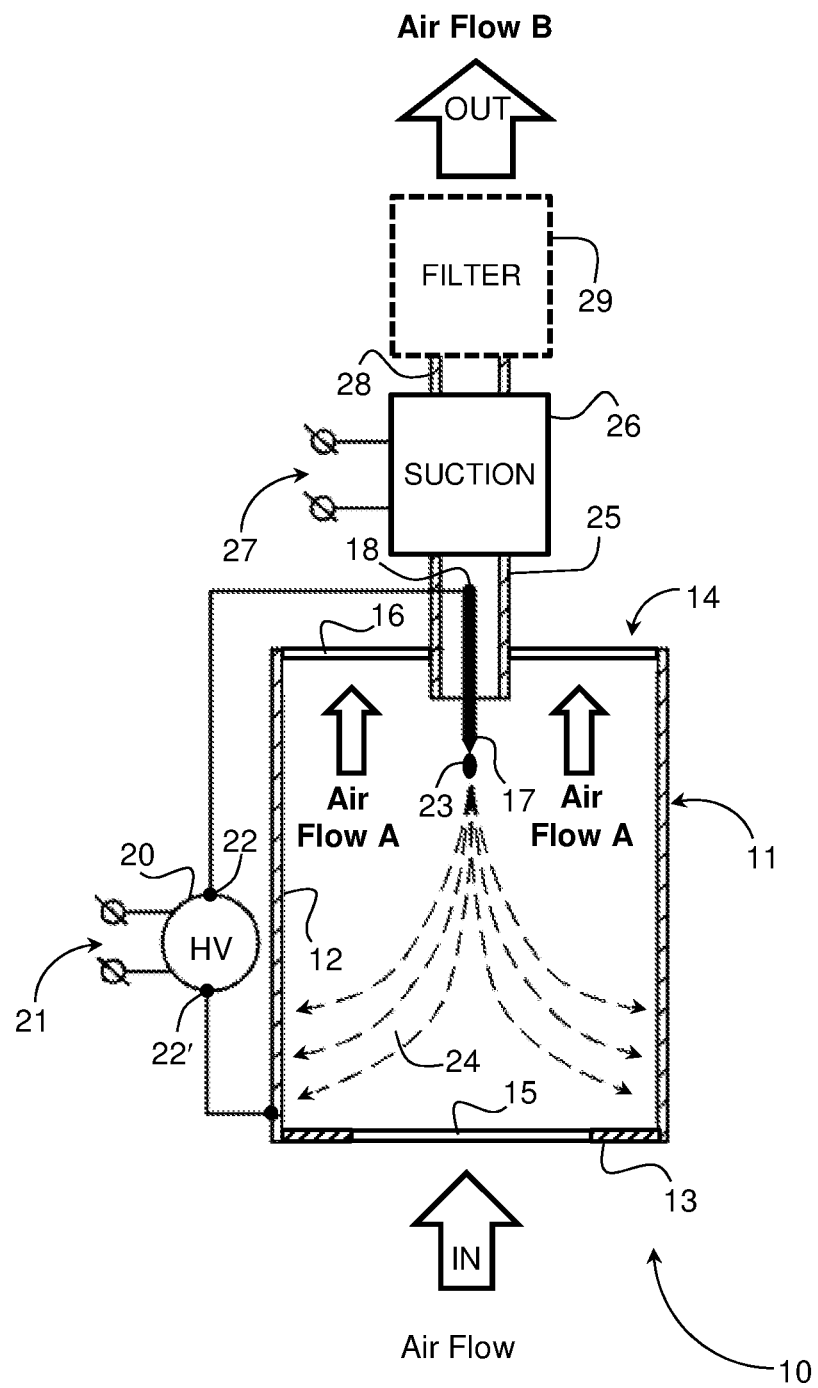

METHOD AND DEVICE FOR OZONE-FREE SEPARATION OF COMPONENTS IN THE CORONA DISCHARGE ZONE

FIELD OF THE INVENTION

The invention relates to air treatment devices that operate using corona discharge. One application relates to a method for air disinfection that uses hydrogen peroxide as a disinfection agent and to a disinfector designated for disinfecting manned premises.

BACKGROUND OF THE INVENTION

Bipolar ion generators have become most commonly used for air disinfection of manned premises. Typical examples are disclosed in U.S. Pat. Nos. 9,071,040, 10,020,180, 10,128,075 and 9,843,169.

The principle of operation of such generators is based on generating a corona discharge area between ionizing electrodes of opposite polarity through which either the entire air-flow containing water molecules (moisture) or a part of it is passed. In known devices the air-flow is either parallel to the axis of the ionizing electrodes and occurs from the non-ionizing part of the electrodes to the ionizing tip thereof (see for example to U.S. Pat. No. 9,843,169) or is perpendicular to the axes of the electrodes, (see U.S. Pat. No. 10,020,180).

In the corona discharge area two processes occur concurrently owing to decomposition of the oxygen molecule $O_2$ into two oxygen atoms O+O i.e. conversion of water molecules $H_2O$ into hydrogen peroxide $H_2O_2$ and also ozone $O_3$ generation, i.e.:

$$H_2O + O = H_2O_2 \quad (1)$$

$$O_2 + O = O_3 \quad (2)$$

Hence the air-flow at the outlet of a bipolar ion generator contains concurrently hydrogen peroxide, ozone and positive and negative ions captured by the air-flow from the corona discharge area. Molecules of $H_2O_2$ used as liquid disinfectant provide longer contact time with bacteria and viruses and spores as compared to gaseous ozone.

A significant drawback of bipolar ionizers is their low disinfection efficiency which is limited by the maximum permitted ozone concentration in manned premises which is equal to 100 ppb.

As noted above $H_2O_2$ and $O_3$ are generated as a result of two concurrent processes in corona discharge. The process of $O_3$ generation is much more efficient than that of $H_2O_2$. Indeed, using current state-of-the-art corona discharge techniques the electrical energy needed to produce 1 kg of ozone is 7-10 kW/h as against 250 kW/h needed to produce 1 kg of $H_2O_2$. However, the maximum permitted ozone concentration in manned premises is only 100 ppb, which establishes a maximum permitted discharge current. In practice this means that taking into account the respective chemical reactions (1) and (2) that produce $H_2O_2$ and $O_3$ by corona discharge, at an energy consumption providing an ozone concentration of 100 ppb, the concentration of $H_2O_2$ is about 7 ppb whereas the maximum permitted concentration of $H_2O_2$ in manned premises is 1000 ppb or 1 ppm.

U.S. Pat. No. 6,373,680 discloses an ionizer device, which reduces the emission of ozone that is produced simultaneously with the ionization process. The device includes a split housing having front and rear sections separated by an active carbon filter and defining front and rear openings. An ionizing electrode is located in the front section and has a tip that faces axially forward toward the front opening surrounding which is an annular non-ionizing electrode. High voltage DC is applied between the two electrodes creates a corona discharge between the tip of the ionizing electrode and the non-ionizing electrode, thus generating a stream of ions and ozone together. An extractor fan located in the rear section applies negative pressure to the interior of the housing, which sucks ozone toward the rear opening, where it is neutralized by the active carbon filter, while allowing the ions to exit through the front opening only.

While the device disclosed in U.S. Pat. No. 6,373,680 separates ozone flow from the ion stream and neutralizes the ozone so that only ions are released, it does not separate hydrogen peroxide from the ozone. Therefore any hydrogen peroxide that is produced in the corona discharge zone will likewise be drawn toward the rear opening by the extractor fan and neutralized by the active carbon filter without exiting through the rear opening into the atmosphere.

Furthermore, most ions created in the corona discharge zone are likewise drawn toward the rear opening under the influence of the extractor fan whose pull exceeds the force of the ion wind directing the escape of ions through the front opening. But in any case, any ions that do escape from the corona discharge area toward the front opening do not form molecules of $H_2O_2$ owing to the absence of secondary emission, which exists only inside the electric field of the corona discharge. So there will be no generation of hydrogen peroxide downstream of the ionizing electrode and the only hydrogen peroxide that is generated will be carried upstream by the extractor fan and neutralized.

Consequently, only a very small number of ions are released into the atmosphere and the device is therefore inefficient as an ion generator and cannot be used at all as a disinfector.

WO2010/123579 discloses a corona gas ionization device in which contaminant byproducts are separated from corona generated ions. The device includes an ion emitter and a non-ionizing reference electrode having two distinct intermediate regions: (a) a plasma region where the corona discharge is formed; and (b) a dark space which is an ion drift region between the glowing plasma region and the non-ionizing reference electrode. Ions and contaminant particles are separated by presenting at least one non-ionized gas stream having a pressure and flowing in a downstream direction while maintaining a lower pressure in the plasma region at the ionizing electrode. The air outlet conveys the clean air in a direction opposite to the ion stream.

EP 2 192 662 discloses a static eliminator comprises an electric discharge portion, and a casing in which the discharge portion for emitting ions in front thereof is disposed. The casing includes an ion emitting opening and an ozone suction opening. Ozone generated in the discharge portion is sucked through the suction opening resulting in sucking air from the ion emitting opening in a direction opposite to that of ion emission through the ion emitting opening.

U.S. Pat. No. 6,508,982 discloses an air-cleaning apparatus and air-cleaning method whereby air is cleaned with an air flow containing ions and ozone generated by corona discharge. The apparatus has a wind tunnel wherein air is sucked in from the distal end thereof and is discharged at an opposite end. A needle electrode is placed in front of the wind tunnel near its axis and corona discharge is induced by applying a high voltage between the needle and an annular electrode surrounding the wind tunnel, generating an air flow containing ions and ozone and thus cleaning air. The wind tunnel serves to increase the flow of air and thereby to enhance the cleansing effect.

SUMMARY OF THE INVENTION

A principal objective of the present invention is to remove the ozone generated in the corona discharge zone so as to prevent its release into an enclosed atmosphere in order to substantially increase the corona discharge current and increase the disinfection efficiency using ion generators, $H_2O_2$ generators and electrostatic filters by more than 10 times.

The invention achieves this objecting using a "tip plane" type corona discharge, wherein according to known corona discharge theory, the corona discharge area consists of a plasma ionizing area which is an irradiant space close to the tip of the ionizing electrode, and a dark area between the ionizing electrode i.e. "the tip" and the non-ionizing electrode i.e. "the plane" where the secondary ion emission occurs in the electrical field of the corona discharge. It should be understood that the principle also applies to the corona discharge and the wire-plane system.

Molecules of water are converted into molecules of $H_2O_2$ during both plasma ionization and the secondary emission processes, i.e. in the entire corona discharge area constituted by both the plasma ionizing area and the dark area, whereas actually the entire amount of ozone is formed in the plasma ionizing area which occupies a very small volume (2-3 mm$^3$) as compared to the entire ozone discharge area.

However owing to the high velocity of the ions in the electrical field of the corona discharge, neutral ozone molecules generated in the plasma ionization region are attracted by the ordered movement of ions along the electric field lines and reach the dark area of the corona discharge. This phenomenon is called ionic wind the speed of which is 1-5 m/s depending on the velocity of the corona discharge current, which is itself a function of the magnitude of the corona discharge current.

The essence of the invention is based on separating the $H_2O_2$ molecules from the molecules of $O_3$ in the corona discharge followed by ozone removal or destruction.

The objective of the invention is achieved by a method and device having the features of the respective independent claims.

The principle of the invention resides in dividing the air-flow entering the corona discharge area into two streams, the first being passed through the plasma area of the corona discharge and an ozone filter while the second is passed through the dark area thereof.

For efficient separation between molecules of $H_2O_2$ and $O_3$ the ionic wind effect should be neutralized, so one of the requirements for implementation of the method that the velocity of the air-flow passed through the plasma area of the corona discharge be higher than the ionic wind velocity.

In an embodiment of the invention, this requirement is fulfilled by mounting the ionizing electrode in a specific location inside the entire air-flow.

According to the invention, the air-flow passing through the corona discharge area is parallel to the axis of the ionizing electrode, but is directed from the tip of the ionizing electrode to its non-ionizing part. This leads to a decrease in the ion wind velocity owing to the opposing directions of the vectors of the ion wind and the air-flow, and as a result to a decrease in the required value of the negative pressure gradient required to separate the flow. In practice, this means that a low power suction device can be used.

Since the ionic wind velocity is in direct proportion to the magnitude of the corona discharge current and in inverse proportion to the volume of the corona discharge area, the second requirement for efficient separation between $H_2O_2$ and $O_3$ is to increase the volume of the corona discharge area.

To comply with this requirement, the non-ionizing electrode is formed as a hollow cylinder with air-flow inlet and outlet apertures inside and the ionizing electrode mounted inside it with its axis coaxial with the geometrical axis of the cylinder.

This solution provides maximum possible volume of the corona discharge area and consequently minimum possible ionic wind velocity.

The method can be applied also to generate both a unipolar negative or positive corona discharge using a single ionizing electrode and to generate a bipolar corona discharge using two ionizing electrodes of opposite polarity. In the latter case the corona discharge will have two plasma corona discharge areas from which to remove ozone.

A disinfector according to the invention is based on the proposed method contains the following elements: a non-ionizing cylindrical electrode with air-flow inlet and outlet apertures, an ionizing electrode, whose axis is coaxial with the geometrical axis of the non-ionizing electrode, a high voltage generator configured to generate a corona discharge area between the electrodes, a suction device having inlet and outlet air channels to generate a negative pressure gradient area in order to form an air-flow passing through the plasma area of the corona discharge and an ozone filter for preventing the escape of ozone.

The inlet aperture of the inlet air-channel of the suction device is positioned close to the ionizing tip of the ionizing electrode, whereas the outlet air channel of the device is connected to the inlet of the ozone filter.

At the same time the high voltage output of the high voltage generator is connected to the ionizing electrode and the low voltage output thereof is connected to the non-ionizing electrode.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 is a schematic representation of a device according to the invention.

DETAILED DESCRIPTION

FIG. 1 shows schematically a disinfector 10 comprising a generally hollow cylindrical chamber 11 having an electrically conductive inner wall 12. The cylinder 11 defines least one air inlet aperture 15 at its lower end 13 and an air outlet aperture 16 at its upper end 14. An ionizing electrode 17 is supported by a non-ionizing part 18 at the upper end 14 of the chamber so that its tip protrudes inside the chamber.

A high voltage generator 20 has supply terminals 21 for connecting to a voltage source such as a main electricity supply and has high voltage output terminals 22, 22' respectively connected to the ionizing electrode 17 and the inner wall 12 of the chamber 11, which serves as a non-ionizing electrode. The application of high voltage across the two electrodes forms a corona discharge area between them, consisting of a plasma corona discharge area 23 and a dark corona discharge area 24. A hollow air-channel 25 is mounted in spatial relationship with the chamber 11 in axial alignment with the ionizing electrode 17 and is dimensioned to cover the whole area of the plasma corona discharge area 23. It is to be understood that the FIGURE is schematic and is intended to demonstrate the principles of the invention. The air-channel 25 may be supported in a lid (not shown) of the chamber that is attached to a rim of the chamber but which is perforated to allow the free flow of air other than the air which passes through the hollow air-channel 25. Alternatively, the chamber 11 and the hollow air-channel 25 may both be supported in proper spatial alignment within an outer structure (not shown). Also, while the device is depicted in the FIGURE as symmetrical with the hollow chamber 11 coaxial with the longitudinal axis of the chamber 11, this is not a requirement. The only requirement is that the ionizing electrode be coaxial with the hollow air-channel 25. Likewise, although the chamber 11 is described as circularly cylindrical, its cross-section can be of any other polygonal shape.

A suction device 26 having power supply input terminals 27 is mounted on top of the air-channel 25 in fluid communication therewith and is likewise coupled via a channel 28 to a filter 29, which is typically an activated carbon (AC) filter. The suction device 26 may be a centrifugal fan or a compressor that creates a negative pressure gradient whereby air in the plasma corona discharge area 23 is drawn through the air-channel 25 into the filter 29. The magnitude of the negative pressure gradient required to remove the ozone may be determined experimentally by measuring the maximum possible concentration of ozone when the corona discharge current is at its maximum and the speed of undivided air flow is at its minimum. The maximum desired corona discharge current is selected based on the use of the device i.e. whether its primary use is to emit hydrogen peroxide and, if so, at what desired concentration; or whether the device is an electrostatic filter or ionizer. Once the maximum desired corona discharge current is established, the air flow is increased and the ozone concentration is measured. The air flow is then increased slightly and the ozone concentration is measured again. This is repeated until the ozone concentration no longer increases. Increasing the air flow beyond this value is to no further benefit and establishes the optimum air flow for the prescribed corona discharge current wherein the velocity of the air flowing through the plasma area of the corona discharge is higher than the ion wind velocity for the preset corona discharge current.

Operation of the disinfector 10 is as follows:

As voltage is applied to the terminals 21 of the high voltage source 20, a corona discharge area is generated between the ionizing electrode 17 and the non-ionizing electrode constituted by the inner wall 12 of the chamber 11. Plasma corona discharge 23 is generated close to the tip of the ionizing electrode 17, while the remaining volume of the corona discharge constitutes the dark corona discharge area 24. At the same time, power is applied to the supply terminals 27 of the suction device 26, thus generating a negative pressure gradient in the air-channel 25, which draws ozone formed in the plasma corona discharge area 24 through the channel 28 to the filter 29 where it is neutralized. Ozone-free air now exits from the ozone filter and reaches the air to be disinfected.

In the air flowing through the dark area of the corona discharge 24 some of the water molecules are converted to hydrogen peroxide molecules due to the interaction with ions in the corona discharge electric field and also reach the environment with the air flowing via the outlet aperture 16 in the lid 14 as shown by arrows A.

As a result, the ozone is separated from most of the hydrogen peroxide, of which a small amount will also pass through the air channels 25 and 28 and will be neutralized by the filter 29. However, the majority of the hydrogen peroxide passes through the outlet aperture 16 into the atmosphere, which is therefore disinfected, while ozone-free air passes into the atmosphere from the filter outlet. Since the ozone is prevented by the filter from escaping into an enclosed atmosphere, the corona discharge current can be safely increased to a level which generates a much higher quantity of hydrogen peroxide as evidenced by Table 1 below showing the technical specification of a disinfector manufactured and tested according to the invention.

The filter 29 in effect neutralizes the ozone in order that the concentration of ozone released into an enclosed atmosphere in which the device is deployed will be below the permitted maximum. However, the same objective can be achieved without the filter by conveying the ozone out of the enclosed atmosphere through an exit tube or pipe that may simply be envisaged as an extension of the channel 28.

TABLE 1

| | | |
|---|---|---|
| 1 | Diameter of the inlet hole of air channel 11 | 8 mm |
| 2 | Distance between the tip of electrode 17 and the inlet aperture of the air-channel 25 | 3 mm |
| 3 | Air-flow velocity in channel 25 | 8 m/sec |
| 4 | Diameter of the non-ionizing electrode (i.e. wall 12) | 40 mm |
| 5 | Corona discharge type | Negative |
| 6 | Corona discharge current | $10^{-2}$ mA |
| 7 | The tested room volume | 7 m$^3$ |
| 8 | H$_2$O$_2$ concentration | 15 ppb |
| 9 | O$_3$ concentration | 5 ppb |

The following devices were used to measure the H$_2$O$_2$ and O$_3$ concentration:

a) For H$_2$O$_2$ concentration: Portable gas detector OC-905
Resolution—0.01 ppm, precision ± 3%
For O$_3$ concentration:
Ozone analyzer Dasibi Model 1008.
Resolution—1 ppb, precision ± 2%.

Although the invention has been described with particular reference to a disinfection device and method, it will be appreciated that the principles of the invention are equally applicable for other devices based on corona discharge where the maximum permissible concentration of ozone limits the efficiency. Thus, the same principles may also be applied to electrostatic filters and ionizers.

It should also be noted that while the ozone filter has been described with regard to an active carbon filter, the term "filter" is to be construed in its broadest sense as a device that separates the ozone from the air and prevents it from escaping into the atmosphere. Whether the ozone is merely trapped or destroyed is not crucial to the invention, because once its passage into the atmosphere is prevented the corona discharge current can safely be increased. Other approaches to preventing the ozone from escaping into the atmosphere include chemical oxidation where the ozone is passed through a titanium reaction chamber. It is also known to use catalytic processes involving reactions with chlorine, bromine, nitrogen, hydrogen, and oxygen gases or a destruction catalyst such as a mixture of copper and manganese dioxides.

The invention claimed is:

1. A method for efficient production of unipolar ions in a corona discharge zone, said method including:
   (a) passing an air stream containing water molecules between at least one ionizing electrode and at least one non-ionizing electrode;
   (b) applying high voltage to said electrodes to create a corona discharge zone consisting of a plasma region wherein ozone is formed and a dark corona discharge region where predominantly hydrogen peroxide is formed;
   (c) dividing an air flow entering the corona discharge zone into two separate air flows, a first of which passes through the corona discharge plasma region, and a second of which passes through the dark corona discharge region; and
   (d) applying a negative pressure gradient to the plasma region to remove the ozone and prevent escape of the ozone into an enclosed atmosphere;
   characterized by:
   (e) supporting the at least one ionizing electrode at the upper end of a chamber whose inner wall surface serves as the non-ionizing electrode with a non-ionizing part of the at least one ionizing electrode in axial alignment with a hollow air-channel dimensioned to cover the whole area of the plasma region so that a tip of the at least one ionizing electrode protrudes out of an open lower end of the air-channel into the chamber, and
   (f) applying a unipolar negative or positive corona discharge between the at least one ionizing electrode and the non-ionizing electrode.

2. The method according to claim 1, wherein the air flow passes though the corona discharge plasma region is generally parallel to the at least one ionizing electrode axis and occurs from a tip of the at least one ionizing electrode towards a non-ionizing part thereof.

3. The method according to claim 1, wherein the directions of the first separate air flow and the second separate air flow coincide.

4. The method according to claim 3, wherein the chamber is circularly cylindrical and the first separate air flow is coaxial with a geometrical axis of the chamber.

5. The method according to claim 1, wherein preventing escape of the ozone in the first air flow into an enclosed atmosphere includes filtering the ozone.

6. The method according to claim 1, wherein preventing escape of the ozone in the first separate air flow into an enclosed atmosphere includes conveying the ozone out of the enclosed atmosphere.

7. The method according to claim 1, including disinfecting air in the enclosed atmosphere by releasing hydrogen peroxide formed in the dark area of the corona discharge into the enclosed atmosphere through at least one air outlet.

8. The method according to claim 1, including purifying air in the enclosed atmosphere by releasing ions formed in the dark area of the corona discharge into the enclosed atmosphere through at least one air outlet.

9. A device comprising:
   a chamber having a first end and a second end opposite the first end,
   a first outlet and a second outlet,
   at least one ionizing electrode supported within the second outlet and having a tip,
   at least one non-ionizing electrode inside the chamber,
   a high voltage generator coupled to said electrodes so as to generate between the electrodes a corona discharge zone having a plasma area wherein ozone is formed and a dark area where predominantly hydrogen peroxide is formed, the first outlet being fluidly coupled to the dark area,
   an air inlet formed in the first end of said chamber for conveying an air flow through the corona discharge zone,
   a suction device coupled to the second outlet for generating negative pressure gradient to the plasma area, and
   the suction device having an outlet through which ozone is discharged and prevented from escaping into an enclosed atmosphere;
   characterized in that:
   the first outlet and the second outlet are formed in the second end of the chamber,
   the second outlet is a hollow air-channel mounted in spatial relationship with the chamber and is dimensioned to cover the whole area of the plasma area,
   the at least one ionizing electrode is supported by a non-ionizing part at the upper end of the chamber in axial alignment with the hollow air-channel so that said ionizing electrode tip protrudes out of an open lower end of the hollow air-channel into the chamber,
   an internal wall of the chamber serves as the non-ionizing electrode whereby the corona discharge zone extends from the tip of the at least one ionizing electrode to the internal wall of the chamber, and
   the high voltage generator is configured to apply a unipolar negative or positive corona discharge between the at least one ionizing electrode and the non-ionizing electrode.

10. The device according to claim 9, where the first air outlet is proximate the at least one ionizing electrode outside the corona discharge zone.

11. The device according to claim 9, wherein the first and second air outlets are disposed opposite to the air inlet.

12. The device according to claim 9, wherein the chamber is cylindrical and the non-ionizing electrode is an inner wall of the chamber, wherein the at least one ionizing electrode is mounted inside the chamber coaxially.

13. A disinfector comprising the device according to claim 9.

14. A unipolar ion generator comprising the device according to claim 9.

15. An electrostatic filter comprising the device according to claim 9.

16. The device according to claim 9, wherein the outlet of the suction device is fluidly coupled to a filter (29) for preventing escape of the ozone into an enclosed atmosphere.

17. The device according to claim 9, wherein the outlet of the suction device is fluidly coupled to an exit tube or pipe for discharging the ozone external to the enclosed atmosphere.

* * * * *